United States Patent
Albonetti et al.

(10) Patent No.: US 6,956,004 B2
(45) Date of Patent: Oct. 18, 2005

(54) VANADIUM/PHOSPHORUS MIXED OXIDE CATALYST

(75) Inventors: Stefania Albonetti, Imola (IT); Fabrizio Cavani, Modena (IT); Simone Ligi, Montefelcino (IT); Gianluca Mazzoni, Torre Boldone (IT)

(73) Assignee: Lonza S.p.A., Milan (IT)

( * ) Notice: Subject to any disclaimer, the term of this patent is extended or adjusted under 35 U.S.C. 154(b) by 19 days.

(21) Appl. No.: 10/779,684

(22) Filed: Feb. 18, 2004

(65) Prior Publication Data

US 2004/0162217 A1 Aug. 19, 2004

Related U.S. Application Data

(62) Division of application No. 09/979,920, filed as application No. PCT/EP00/04939 on May 30, 2000, now Pat. No. 6,734,135.

(30) Foreign Application Priority Data

Jun. 1, 1999 (IT) .......................... MI99A1233

(51) Int. Cl.$^7$ ............................ B01J 21/18; B01J 27/14; C07D 307/34; C07D 307/60
(52) U.S. Cl. ................ 502/182; 502/209; 549/256; 549/259; 549/233; 549/260; 549/262
(58) Field of Search .............................. 502/182, 209; 549/256, 259, 233, 260, 262

(56) References Cited

U.S. PATENT DOCUMENTS

| 4,594,433 A | 6/1986 | Suciu et al. |
| 4,668,652 A | 5/1987 | Fumagalli et al. |
| 5,032,564 A | 7/1991 | Kiyoura et al. |
| 5,137,860 A | 8/1992 | Ebner et al. |
| 5,847,163 A | * 12/1998 | Mazzoni et al. ............ 549/259 |

FOREIGN PATENT DOCUMENTS

| EP | 0384749 | 2/1990 |
| EP | 0520972 | 3/1992 |
| EP | 0804963 | 4/1997 |
| WO | WO 96/25230 | 8/1996 |

OTHER PUBLICATIONS

A copy of applicant's International Search Report from their PCT application, dated Feb. 11, 2000.

* cited by examiner

*Primary Examiner*—Elizabeth D. Wood
(74) *Attorney, Agent, or Firm*—Fisher Christen & Sabol

(57) ABSTRACT

Active vanadium/phosphorus mixed oxide catalyst for the conversion of non-aromatic hydrocarbons, e.g., n-butane, into maleic anhydride. The catalyst is prepared from the catalyst precursor, that is, prepared by the reaction of a source of vanadium in an organic medium in the presence of a phosphorus source. The organic medium is (a) isobutyl alcohol or a mixture of isobutyl alcohol and benzyl alcohol and (b) a polyol. The catalyst precurso is transformed into the active catalyst by an activation process that includes a heat treatment that includes applying a temperature of up to 600° C.

22 Claims, No Drawings

VANADIUM/PHOSPHORUS MIXED OXIDE CATALYST

This is a division of U.S. patent application Ser. No. 09/979,920, filed on Apr. 4, 2002, now U.S. Pat. No. 6,734,135, issued on May 11, 2004, that is a 371 of International Patent Application PCT/EP00/04939, filed on May 30, 2000, which has priority benefit on Italian Patent Application MI99A001233, filed on Jun. 1, 1999.

The invention relates to a process for the production of a vanadium/phosphorus mixed oxide catalyst precursor, its transformation into the active catalyst and a process for the production of maleic anhydride using this catalyst.

Maleic anhydride is a well known and versatile intermediate for manufacturing unsaturated polyester resins, pharmaceuticals or agrochemicals. It is usually produced by catalytic partial oxidation of aromatic (benzene) or non-aromatic (n-butane) hydrocarbons.

The main component of the active catalyst in the oxidation of non-aromatic hydrocarbons like n-butane to maleic anhydride is vanadyl pyrophosphate, $(VO)_2P_2O_7$, which as a rule is obtained by thermal treatment of vanadyl acid orthophosphate hemihydrate of the formula $(VO)HPO_4.0.5H_2O$, acting as catalyst precursor. Both vanadyl pyrophosphate and vanadyl acid orthophosphate hemihydrate may, if desired, be accompanied by a promoter element selected from the groups IA, IB, IIA, IIB, IIIA, IIIIB, IVA, IVB, VA, VB, VIA, VIB and VIIIA of the periodic table of elements, or mixtures of such elements Methods for preparing the precursor compound conventionally involve reducing a pentavalent vanadium compound under conditions which will provide vanadium in a tetravalent state (average oxidation number +IV).

Prior art knows a great many different procedures, which however in general involve the use of vanadium pentoxide ($V_2O_5$) as a source of pentavalent vanadium and orthophosphoric acid ($H_3PO_4$) as the phosphorus source (see e.g. U.S. Pat. No. 5,137,860 or EP-A-0 804 963).

As a reducing agent in principle any inorganic or organic compound containing elements which are able to act as a redox couple possessing an oxidation potential suitable for this kind of reaction may be suitably applied.

The most common reducing agent is hydrogen chloride in aqueous solution.

Also favourably applied are organic media like primary or secondary aliphatic alcohols or aromatic alcohols such as benzyl alcohol as these compounds seem to at least in part dissolve the reactants and thereby facilitate the redox reaction.

The most preferred organic reducing agent is isobutyl alcohol as isobutyl alcohol combines optimal characteristics such as (i) a boiling point of 108° C. at atmospheric pressure, (ii) dissolution of the vanadium alcoholates formed from $V_2O_5$, thus favouring a complete redox reaction in the liquid phase and (iii) achieving a redox potential for the couples isobutyl alcohol/isobutyraldehyde and isobutyl alcohol/isobutyric acid suitable to let the alcohol act as reducing agent. The tetravalent vanadium reacts with phosphoric acid ($H_3PO_4$) and leads to precipitation of the precursor vanadyl acid orthophosphate hemihydrate of the formula $(VO)HPO_4.0.5H_2O$. The precipitate is usually washed with isobutyl alcohol and subsequently dried.

A major disadvantage of the conventional method as described above is that even after drying the precursor contains some percent of organic compounds from the organic reaction medium, compounds which are supposedly either (i) strongly adsorbed at the solid surface, and therefore not easily removable by the washing and drying treatment, or (ii) physically trapped in between the crystals of the precursor, or (iii) physically or chemically trapped ("intercalated") in the crystalline structure of the precursor.

It has been found that this percentage of organic compound which remains trapped in the precursor is a fundamental parameter which can adversely affect the performance characteristics of the active catalyst obtained after the thermal treatment.

The object of the present invention therefore was to provide a method for controlling the carbon content in a vanadium/phosphorus mixed oxide catalyst precursor and accordingly to provide a superior catalyst precursor which, when activated, leads to superior results in the conversion of a non-aromatic hydrocarbon to maleic anhydride.

It was found that the objectives could be achieved with a new process for the preparation of a vanadium/phosphorus mixed oxide catalyst precursor according to claim 1.

The invention comprises reducing a source of vanadium in the presence of a phosphorus source in an organic medium which comprises
(a) isobutyl alcohol or a mixture of isobutyl alcohol and benzyl alcohol and
(b) a polyol in the weight ratio of 99:1 to 5:95.

In a mixture of isobutyl alcohol and benzyl alcohol the benzyl alcohol content is as a rule between 5 and 50 wt. %.

As a source of vanadium a tetravalent or pentavalent vanadium compound may be applied. Representative examples, although not limiting, are vanadium tetrachloride ($VCl_4$), vanadium oxytribromide ($VOBr_3$), vanadium pentoxide ($V_2O_5$), vanadyl phosphate ($VOPO_4.n\ H_2O$) and vanadium tetraoxide ($V_2O_4$). Vanadium pentoxide is the preferred vanadium source. As mentioned above, the vanadium source may, if desired, be accompanied by promoter elements selected from the groups IA, IB, IIA, IIB, IIIA, IIIIB, IVA, IVB, VA, VB, VIA, VIB and VIIIA of the periodic table of elements, or mixtures thereof. Preferred promoter elements are selected from the group consisting of zirconium, bismuth, lithium, molybdenum, boron, zinc, titanium, iron and nickel.

Orthophosphoric acid ($H_3PO_4$) is the preferred phosphorus source.

Isobutyl alcohol is the preferred component (a).

Polyols which can be used as the component (b) are expediently $C_{2-6}$ aliphatic polyols, preferably $C_{2-6}$-alkanediols such as 1,2-ethanediol, 1,2-propanediol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol and 3,4-hexanediol.

Most preferred polyols are the $C_{2-4}$-alkanediols 1,2-ethanediol, 1,3-propanediol and 1,4-butanediol.

The preferred mixture of alcohols contains 5 to 30 mol % of polyol with repect to isobutyl alcohol.

As a rule the vanadium source together with the phosphorus source is suspended in the organic medium and the mixture is kept under agitation at a temperature of expediently 90° C. to 200° C., preferably 100° C. to 150° C. over a period of 1 h to 24 h.

The ratio of vanadium source to phosphorus source is conveniently such that the P/V atomic ratio is in the range of 1:1 to 1.3:1, preferably 1.1:1 to 1.2:1.

As a rule after the reduction the precursor vanadyl acid orthophosphate hemihydrate of the formula $(VO)HPO_4.0.5H_2O$ is formed which is filtered, washed and subsequently dried at a temperature of expediently 120° C. to 200° C.

Due to the reduction treatment according to the invention the carbon content of the precursor can be controlled in the range of 0.7 wt. % to 15.0 wt. %, preferably in the range of 0.7 wt. % to 4 wt. %.

It has been found that best results are obtained with catalyst precursors which, after an additional thermal treatment at about 300° C. for about 3 hours in air have a residual carbon content of 0.7 wt. % to 3 wt. %, most preferably 0.8 wt. % to 1.5 wt. %.

Once prepared the precursor can in view of its further activation treatment be formed into defined structures with defined properties. Such procedures may include wet grinding to a specific particle size, the addition of additives to improve attrition resistance, and the formation of a convenient shape.

A spherical shape for instance is most suitable for the application of the catalyst in a fluidized bed.

The further transformation of the so formed precursor into the active catalyst can be performed following a great number of activation processes known in the art, but in general include a heat treatment applying temperatures of up to 600° C. More in detail, these processes may involve:

(a) an initial heating of the precursor to a temperature not to exceed 250° C.
(b) a further heat treatment from about 200° C. to at least 380° C. to 600° C. at the maximum
(c) maintaining the temperature of stage (b) over a certain time and
(d) cooling the activated catalyst, thereby maintaining an individually controlled atmosphere in all steps.

In a preferred embodiment, the activation of the precursor is accomplished using the procedure described in EP-A-0 804 963.

In a more preferred embodiment, the activation comprises the steps of
(a) heating the catalyst precursor from room temperature to a precalcination temperature of about 300° C. in air or oxygen-depleted air
(b) keeping at said precalcination temperature,
(c) further heating the precalcined catalyst precursor in nitrogen up to a calcination temperature of about 550° C. and
(d) keeping at said calcination temperature.

After the transformation into the active catalyst the catalyst is ready to be applied for the conversion of non-aromatic hydrocarbons to maleic anhydride.

Such processes are well known in the art, e. g. from U.S. Pat. No. 4,594,433, U.S. Pat. No. 5,137,860 or U.S. Pat. No. 4,668,652.

In general the non-aromatic hydrocarbon is converted with oxygen or an oxygen containing gas at a temperature from about 320° C. to 500° C. to maleic anhydride. The non-aromatic hydrocarbon is expediently selected from aliphatic $C_{4-10}$ hydrocarbons, preferably n-butane. The conversion can take place in a fixed bed or a fluidized bed reactor but preferably in a fluidized bed reactor. The following examples are given by way of illustration only and are not construed as to in any way limit the invention.

EXAMPLES

The following examples, the carbon content was determined by combustion in pure oxygen at high temperature using the apparatus and procedure described below and detection of the carbon dioxide formed by infrared analysis.
Apparatus: ELTRA 900CS
Measuring range: 0.001–100 wt. % C
Sensitivity: 0.0001 wt. % C
Time per sample: 90 s
Sample size: 0.1–0.5 g
Oven temperature: 400–1500° C.
Oxygen purity: 99.5% min.
Oxygen flow rate: 4 l/min
Procedure:

The furnace was heated up to 1330° C. and oxygen flow was opened 10 minutes before starting the analysis. High carbon content detector was selected and calibrated with standard samples having known carbon content. The sample size used was 150±10 mg.

Comparative Example 1 (Following Example 1 (Comparison) of EP-A 0 804 963)

Into a three-necked 1-1 flask fitted with thermometer, mechanical stirrer and packed glass distillation column with reflux condenser and water separator (cf. example 5), were introduced 8.20 g of $V_2O_5$ and 10.1 g of $H_3PO_4$ (100%), suspended in 75 ml of isobutyl alcohol (99%+).

The mixture was then kept under agitation and heated up to reflux and left at these conditions for 6 h. The colour of the mixture changed from red-brown to dark green and then finally to bright blue.

The mixture was cooled to room temperature, then filtered and washed with a large excess of isobutyl alcohol. The solid was then dried in air at 125° C. for 5 h. The carbon content of the dried precipitate was 0.6 wt. %.

The solid was then treated in air by heating from room temperature to 300° C. (heating rate 1 K/min), then left at 300° C. for 6 h, heated in $N_2$ up to 550° C. (heating rate 1 K/min) and finally left at 550° C. for 6 h. After the precalcination step (in air at 300° C.), the residual carbon content was 0.5 wt. %.

Comparative Example 2

The preparation of the precursor was done as described in comparative example 1, but the thermal treatment was done according to the procedure of example 4 of EP-A-0 804 963:
(a) heating in air from 25° C. to 180° C. at heating rate of 4 K/min
(b) further heating from 180° C. to 425° C. in a mixture of air (70% vol) and steam (30% vol) at a heating rate of 1.5 K/min
(c) isothermal step at 425° C. in the same atmosphere as in step (b), for 2 h
(d) isothermal step at 425° C. in an atmosphere of nitrogen (70% vol) and steam (30% vol) for 3 h
(e) cooling in a mixture of nitrogen and steam at a rate of −2 K/min.

Comparative Example 3

The preparation of the precursor was done as described in comparative example 1, but the isobutyl alcohol was replaced by 35.5 g of 1,3-propanediol.

The dried catalyst precursor had a carbon content of 11.6 wt. %.

The activation was performed according to the procedure of comparative example 1.

Example 1

4.11 g of $V_2O_5$ and 5.11 g of $H_3PO_4$ (100%) were suspended in 37.5 ml of a mixture of 1,2-ethanediol/isobutyl alcohol (20/80 v/v). The mixture was kept under agitation and heated up to reflux, and left at these conditions for 6 h. The color of the mixture changed from red-brown to dark green and then finally to bright blue.

The mixture was cooled to room temperature, then filtered and washed with a large excess of isobutyl alcohol. The solid was then dried in air at 125° C. for 5 h.

The dried catalyst precursor had a carbon content of 2.3 wt. %, while after the precalcination treatment in air at 300° C. the amount of residual carbon was 1.2 wt. %.

The activation was performed according to comparative example 1.

Comparative Example 4

The same procedure as in example 1 was carried out, with the exception of 1,2-ethanediol being replaced with benzyl alcohol.

The dried catalyst precursor hat a carbon content of 1.6 wt. % while after precalcination the residual amount of carbon was 0.4 wt. %.

The activation was performed according to the procedure of comparative example 1.

Example 2

8.20 g of $V_2O_5$ and 10.07 g of $H_3PO_4$ (100%) were suspended in 75 ml of a mixture of 1,3-propanediol/isobutyl alcohol (20/80 v/v). The mixture was kept under agitation and heated up to reflux, and left at these conditions for 6 h. The color of the mixture changed from red-brown to dark green and then finally to bright blue.

The mixture was cooled to room temperature, then filtered and washed with a large excess of isobutyl alcohol. The solid was then dried in air at 125° C. for 5 h.

The dried catalyst precursor had a carbon content of 2.8 wt. % while after precalcination the residual amount of carbon was 1.8 wt. %.

The activation was performed according to the procedure of comparative example 1.

Example 3

The procedure of example 1 was repeated, but as reducing agent 37.5 ml of a mixture of 1,4-butanediol/isobutyl alcohol (20/80 v/v) was chosen.

The dried catalyst precursor had a carbon content of 1.6 wt. % while after precalcination the residual amount of carbon was 1.1 wt. %.

The activation was performed according to the procedure of comparative example 1.

Example 4

The procedure of example 1 was repeated, but as reducing agent 37.5 ml of a mixture of 1,3-butanediol/isobutyl alcohol (20/80 v/v) was chosen.

The dried catalyst precursor had a carbon content of 1.6 wt. % while after precalcination the residual amount was 1.4 wt. %.

The activation was performed according to comparative example 1.

Example 5

The procedure of example 3 was repeated (using the apparatus described in comparative example 1), but the water generated during the reaction was partially removed by azeotropic destillation.

The dried catalyst precursor had a carbon content of 2.3 wt. % while after precalcination the residual amount was 1.5 wt. %.

The activation was performed according to comparative example 2.

Catalytic Tests

The catalytic tests were performed at atmospheric pressure in a fixed-bed stainless steel laboratory reactor (length 25.4 cm, diameter 1.27 cm) loaded with 3 g of catalyst. The products were collected and absorbed in anhydrous acetone and analysed by gas chromatography. The performance of the catalyst was determined on the basis of the percent conversion of n-butane fed to the reactor (together with oxygen and helium), the yield of maleic anhydride recovered in the absorber (MA yield) in % and the selectivity of the conversion towards maleic anhydride (MA selectivity) in %.

The following conditions were maintained during the tests:

| | |
|---|---|
| W/F (weight of catalyst/total volumetric flow rate): | 1.3 g · s/ml |
| feed composition: | 1.7% n-butane, 17.2% $O_2$, rest He |
| measurement: | after 200–300 h time-on-stream (stable catalytic performance). |

The results obtained for the various catalysts are summarised in table 1.

TABLE 1

| Example No. | θ [° C.] | Conversion [%] | MA Yield [%] | MA Selectivity [%] |
|---|---|---|---|---|
| Comp. 1 | 360 | 9.8 | 6.4 | 65.3 |
| | 380 | 16.7 | 11.4 | 68.3 |
| | 400 | 26.3 | 17.2 | 65.4 |
| | 420 | 39.5 | 26.1 | 66.1 |
| | 440 | 53.8 | 32.9 | 61.2 |
| Comp. 2 | 360 | 12.2 | 8.7 | 71.3 |
| | 380 | 18.0 | 12.4 | 68.9 |
| | 400 | 26.8 | 18.2 | 67.9 |
| | 420 | 39.6 | 25.5 | 64.4 |
| | 440 | 56.0 | 34.4 | 61.4 |
| | 460 | 71.5 | 40.3 | 56.4 |
| Comp. 3 | 360 | 9.5 | 0.6 | 6.3 |
| | 380 | 30.5 | 2.1 | 6.9 |
| | 400 | 40.6 | 2.3 | 5.7 |
| | 420 | 43.6 | 3.6 | 8.3 |
| Comp. 4 | 360 | 11.1 | 7.5 | 68 |
| | 380 | 17.1 | 11.7 | 68.5 |
| | 400 | 26.5 | 17.5 | 66.2 |
| | 420 | 39.5 | 25.7 | 65 |
| | 440 | 55.1 | 35.0 | 63.5 |
| 1 | 360 | 16.7 | 12.1 | 72.2 |
| | 380 | 34.9 | 24.0 | 68.7 |
| | 400 | 42.3 | 29.7 | 70.2 |
| | 420 | 47.2 | 30.4 | 64.5 |
| 2 | 360 | 20.6 | 15.3 | 74.3 |
| | 400 | 47.6 | 33.9 | 71.2 |
| | 420 | 59.1 | 38.4 | 65.0 |
| 3 | 360 | 39.7 | 27.8 | 70.0 |
| | 370 | 51.9 | 36.0 | 69.4 |
| | 400 | 72.5 | 44.6 | 61.5 |
| | 420 | 84.2 | 44.3 | 52.6 |
| 4 | 360 | 26.0 | 18.7 | 72.1 |
| | 380 | 53.7 | 38.2 | 71.2 |
| | 400 | 67.4 | 44.0 | 65.3 |
| | 420 | 75.3 | 42.8 | 56.8 |
| 5 | 360 | 40.1 | 28.1 | 70.1 |
| | 380 | 57.3 | 39.7 | 69.3 |

TABLE 1-continued

| Example No. | θ [° C.] | Conversion [%] | MA Yield [%] | MA Selectivity [%] |
|---|---|---|---|---|
| | 400 | 72.9 | 45.0 | 61.8 |
| | 420 | 85.3 | 45.2 | 53.0 |

From the examples reported above it is clear that the best performance the highest yield that is obtained for those catalysts. Example 3 and which fulfill both the requirements of having a carbon content in the precursor of 1 to 2 wt. % and a residual carbon content after precalcination at 300° C. in the air of 0.8 to 1.5 wt. %.

What is claimed is:

1. A process for the transformation of a vanadium/phosphorus mixed oxide catalyst precursor into an active vanadium/phosphorus mixed oxide catalyst for the production of maleic anhydride, said transformation process comprising a heat treatment of the catalyst precursor at a temperature of up to 600° C. to provide said active catalyst, said catalyst precursor having been prepared by a process comprising reacting a source of vanadium in an organic medium in the presence of a phosphorus source, the organic medium comprising:
   (a) isobutyl alcohol or a mixture of isobutyl alcohol and benzyl alcohol, and
   (b) a polyol in a weight ratio (a) to (b) of 99:1 to 5:95.

2. The process of claim 1 wherein the heat treatment of the catalyst precursor comprises the steps of:
   (a) heating the catalyst precursor from room temperature to a precalcination temperature of about 300° C. in air or oxygen-depleted air;
   (b) keeping the catalyst precursor at said precalcination temperature;
   (c) further heating the precalcined catalyst precursor in nitrogen up to a calcination temperature of about 550° C.; and
   (d) keeping the precalcined catalyst precursor at said calcination temperature.

3. An active vanadium/phosphorus mixed oxide catalyst for the production of maleic anhydride, that is prepaid by the process of claim 1.

4. A process for the preparation of maleic anhydride, that comprises converting a feeding gas comprising (i) non-aromatic hydrocarbon having a least 4 carbon atoms and (ii) oxygen or an oxygen-containing gas, in the presence of the active catalyst of claim 3 at a temperature of from 320° C. to 500° C.

5. The process of claim 4 wherein the non-aromatic hydrocarbon is n-butane.

6. The process of claim 1, wherein the catalyst precursor has a carbon content in the range of 0 7 wt. % to 15.0 wt. %.

7. The process of claim 1, wherein the catalyst precursor has a carbon content in the range of 0.7 wt. % to 4 wt. %.

8. The process of claim 1, wherein the heat treatment of the catalyst precursor comprises the steps of:
   (a) initially heating the catalyst precursor to a temperature not to exceed 250° C.;
   (b) further heat treating the catalyst precursor from about 200° C. to at least 380° C. to 600° C. at the maximum;
   (c) maintaining the temperature of stage (b) over a certain time; and
   (d) cooling the activated catalyst, thereby maintaining an individually controlled atmosphere in all of the steps.

9. The process of claim 4, wherein the non-aromatic hydrocarbon is an aliphatic-$C_{4-10}$-hydrocarbon.

10. The process of claim 4, wherein the conversion is conducted in a fluidized bed reactor.

11. The process of claim 2, wherein the catalyst precursor has a carbon content in the range of 0.7 wt. % to 3 wt. %.

12. The process of claim 2, wherein the catalyst precursor has a carbon content in the range of 0.8 wt. % to 1.5 wt. %.

13. An active vanadium/phosphorus mixed oxide catalyst for the production of maleic anhydride, that is prepared by the process of claim 2.

14. A process for the production of maleic anhydride, that comprises converting a feeding gas comprising (i) a non-aromatic hydrocarbon having at least 4 carbon atom and (ii) oxygen or an oxygen-containing gas, in the presence of the active catalyst of claim 13 at a temperature from 320° C. to 500° C.

15. The process of claim 14 wherein the non-aromatic hydrocarbon is n-butane.

16. The process of claim 14 wherein the non-aromatic hydrocarbon is an aliphatic-$C_{4-10}$-hydrocarbon.

17. The process of claim 14, wherein the conversion is conducted in a fluidized bed reactor.

18. The active catalyst of claim 3, wherein a promoter element is also present.

19. The active catalyst of claim 13, wherein a promoter element is also present.

20. The active catalyst of claim 3, wherein the active catalyst is in spherical particle shape.

21. The active catalyst of claim 13, wherein the active catalyst is in spherical particle shape.

22. The process of claim 4, wherein the conversion is at least 47.2 percent and the yield of maleic anhydride is at least 30.4 percent.

* * * * *